United States Patent
Boudreau et al.

(10) Patent No.: US 10,094,762 B2
(45) Date of Patent: Oct. 9, 2018

(54) PATTERNED CAPILLARY DEVICE AND PROCESS FOR FABRICATING THEREOF

(71) Applicant: Universite Laval, Quebec (CA)

(72) Inventors: Denis Boudreau, Quebec (CA); Felix-Antoine Lavoie, Quebec (CA); Olivier Ratelle, Saint-Tite (CA)

(73) Assignee: UNIVERSITÉ LAVAL, Quebec (CA)

( * ) Notice: Subject to any disclaimer, the term of this patent is extended or adjusted under 35 U.S.C. 154(b) by 87 days.

(21) Appl. No.: 13/905,992

(22) Filed: May 30, 2013

(65) Prior Publication Data
US 2014/0356937 A1 Dec. 4, 2014

(51) Int. Cl.
G01N 15/00 (2006.01)
B01L 3/00 (2006.01)
G01N 15/14 (2006.01)
G01N 15/10 (2006.01)

(52) U.S. Cl.
CPC ..... *G01N 15/1459* (2013.01); *G01N 15/1436* (2013.01); *G01N 2015/1006* (2013.01); *G01N 2015/1447* (2013.01)

(58) Field of Classification Search
CPC ... G01N 2015/1006; G01N 2015/1447; G01N 15/1459; G01N 15/1436; G01N 21/6486
See application file for complete search history.

(56) References Cited

U.S. PATENT DOCUMENTS

| | | | | |
|---|---|---|---|---|
| 5,514,501 A | * | 5/1996 | Tarlov | B01J 19/0046 427/377 |
| 2002/0025534 A1 | * | 2/2002 | Goh et al. | 435/7.1 |
| 2003/0207257 A1 | * | 11/2003 | Cohen et al. | 435/5 |
| 2005/0014151 A1 | * | 1/2005 | Textor | A61L 27/34 435/6.19 |
| 2007/0000866 A1 | * | 1/2007 | Ryan | B82Y 5/00 216/62 |
| 2009/0036324 A1 | * | 2/2009 | Fan | G01N 33/582 506/9 |
| 2009/0311555 A1 | * | 12/2009 | Badyal et al. | 428/704 |
| 2012/0078531 A1 | | 3/2012 | Lo et al. | |

OTHER PUBLICATIONS

Algar et al. The controlled display of biomolecules on nanoparticles: a challenge suited to bioorthogonal chemistry. Bioconjug Chem. May 18, 2011;22(5):825-58.
Brouard et al. Label-free biosensing based on multilayer fluorescent nanocomposites and a cationic polymeric transducer. ACS Nano. Mar. 22, 2011;5(3):1888-96.
(Continued)

*Primary Examiner* — Nathan A Bowers
(74) *Attorney, Agent, or Firm* — Norton Rose Fulbright US LLP

(57) ABSTRACT

A patterned capillary device comprising a pattern on an inner surface is described herein. More specifically, the patterned capillary device comprises a wall having an outer surface and an inner surface, the wall defining a fluidic channel. A substantially opaque film covers the inner surface of the wall, the opaque film comprising a plurality of substantially transparent segments defining a pattern. A process for fabricating a pattern formed of opaque and transparent portions on an inner surface of a capillary device is also described herein.

14 Claims, 12 Drawing Sheets

(56) References Cited

OTHER PUBLICATIONS

Geng et al. Conjugated Polymer and Gold Nanoparticle Co-loaded PLGA Nanocomposites with Eccentric Internal Nanostructure for Dual-modal Targeted Cellular Imaging. Small. Aug. 6, 2012;8(15):2421-9. Epub Apr. 30, 2012.

Graham et al. Control of enhanced Raman scattering using a DNA-based assembly process of dye-coded nanoparticles. Sep. 2008;3(9):548-51.

Heavens O. Optical Properties of Thin Films. 1960. Rep. Prog. Phys. 23(1), 1-65.

Hu et al. Novel plating solution for electroless deposition of gold film onto glass surface. Surface & Coatings Technology 202 (2008) 2922-2926.

Huang et al. Photopatterning of Self-Assembled Alkanethiolate Monolayers on Gold: A Simple Monolayer Photoresist Utilizing Aqueous Chemistry. Langmuir (1994):626-628.

Jans et al. Dynamic Light Scattering as a Powerful Tool for Gold Nanoparticle Bioconjugation and Biomolecular Binding Studies. Anal. Chem. 2009, 81, 9425-9432.

Kiesel et al. Microfluidic-based detection platform for on-the-flow analyte characterization. Proc. of SPIE vol. 7606 760608-2.

Kiesel et al. Spatially modulated fluorescence emission from moving particles. Applied Physics Letters 94, 041107 (2009).

Liu et al. Gram-Scale Synthesis and Biofunctionalization of Silica-Coated Silver Nanoparticles for Fast Colorimetric DNA Detection. Anal. Chem. 2005, 77, 2595-2600.

Muller et al. Detection of Low Level Cryoglobulins by Flow Cytometry. Cytometry Part A 81A: 883-887 (2012).

Pei et al. Designed Diblock Oligonucleotide for the Synthesis of Spatially Isolated and Highly Hybridizable Functionalization of DNA-Gold Nanoparticle Nanoconjugates. J. Am. Chem. Soc. 2012, 134, 11876-11879.

Resch-Genger. Quantum dots versus organic dyes as fluorescent labels. Nature Methods | vol. 5 No. 9 | Sep. 2008.

Smith, R.A., Giorgio, T. D. Quantitative Measurement of Multifunctional Quantum Dot Binding to Cellular Targets Using Flow Cytometry. Cytometry Part A, 75A: 465-474, 2009.

Tavares et al. On-Chip Transduction of Nucleic Acid Hybridization Using Spatial Profiles of Immobilized Quantum Dots and Fluorescence Resonance Energy Transfer. Anal. Chem. 2012, 84, 312-319.

You et al. Self-Controlled Monofunctionalization of Quantum Dots for Multiplexed Protein Tracking in Live Cells. Angew. Chem. Int. Ed. 2010, 49, 4108-4112.

Yun et al. Simultaneous counting of two subsets of leukocytes using fluorescent silica nanoparticles in a sheathless microchip flow cytometer. Lab Chip, 2010, 10, 3243-3254.

\* cited by examiner

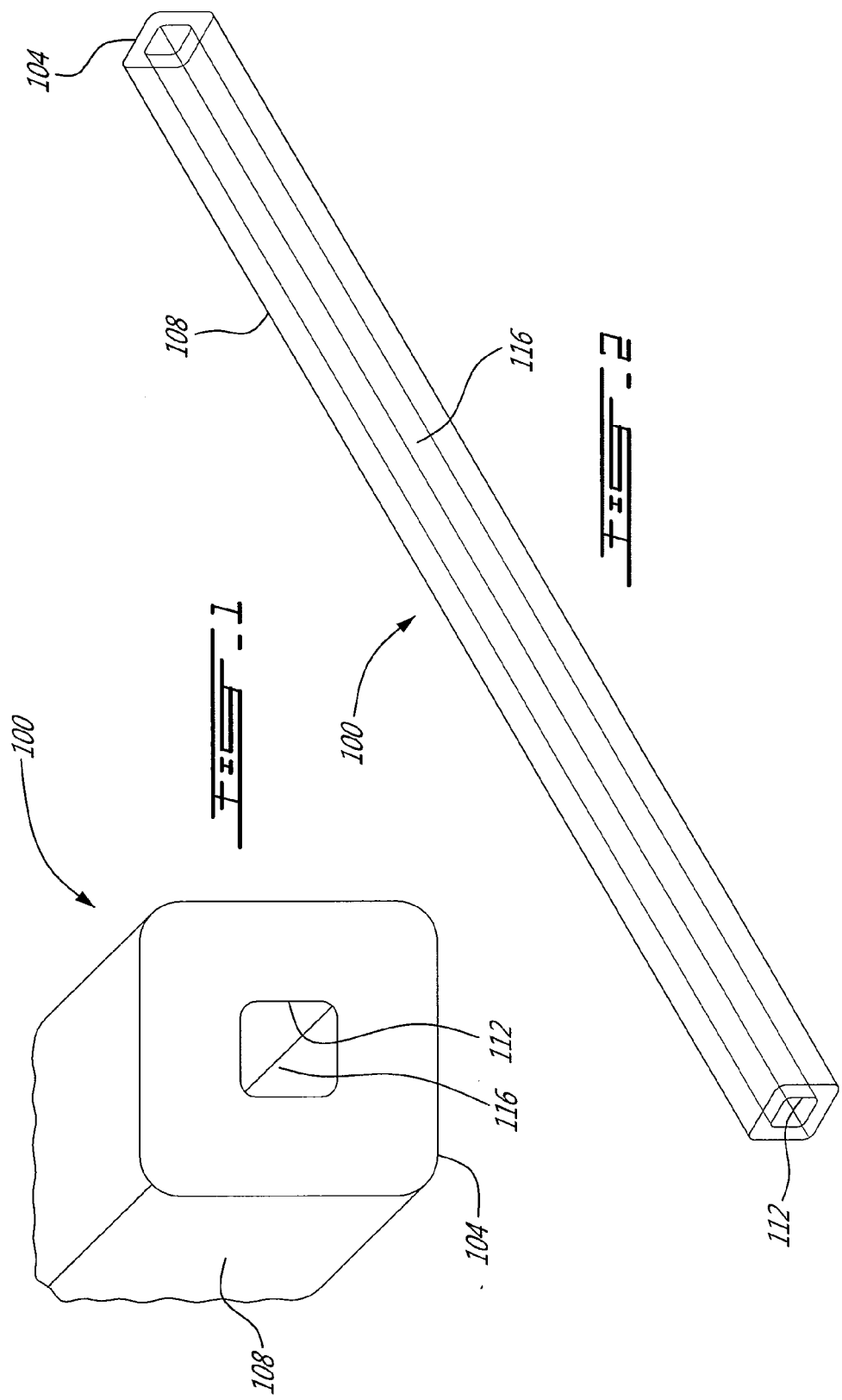

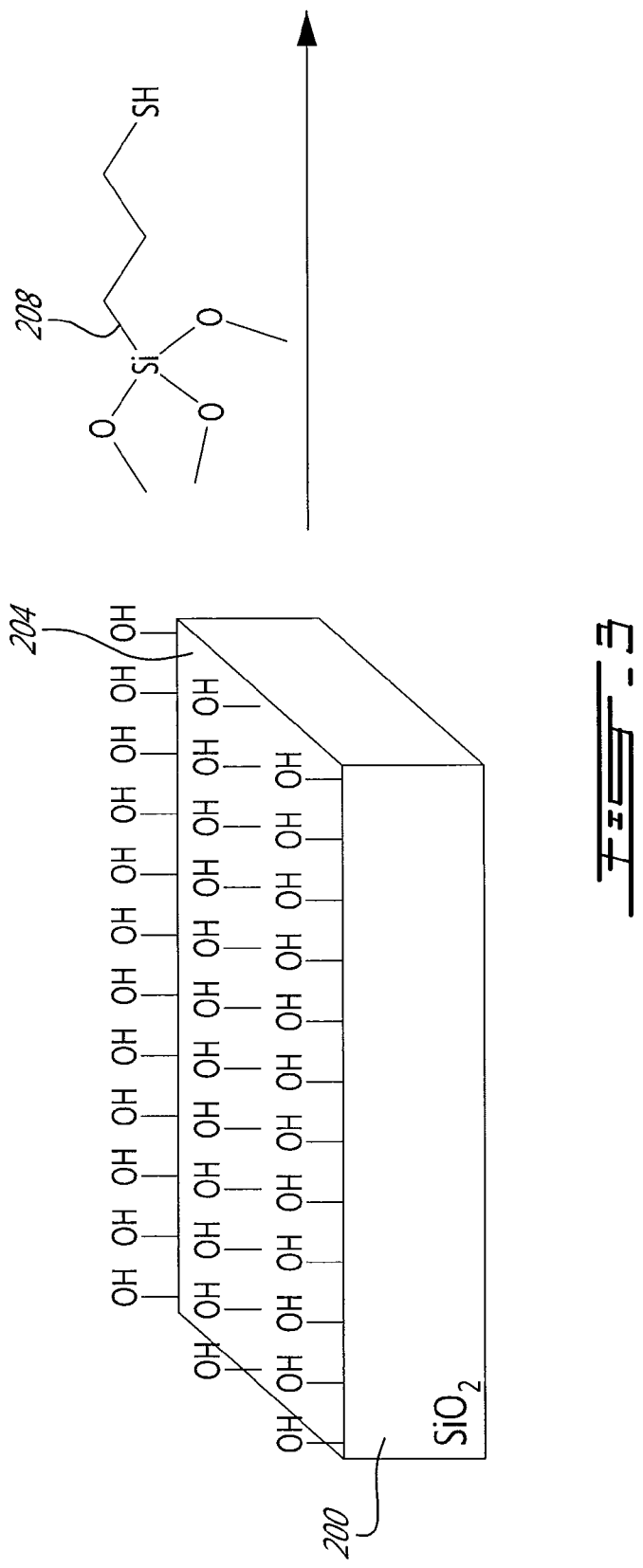

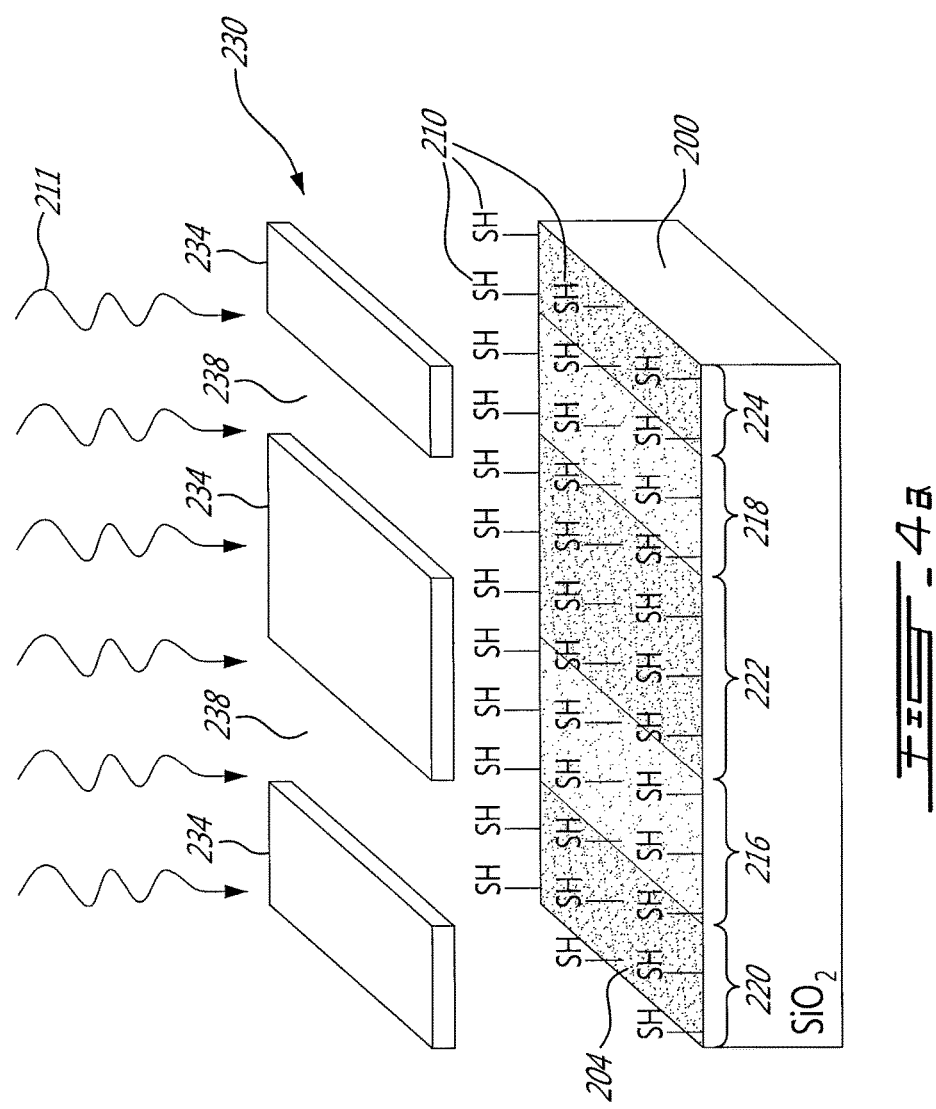

PATTERNED CAPILLARY DEVICE AND PROCESS FOR FABRICATING THEREOF

FIELD

The present subject-matter broadly relates to a barcoded capillary device and for fabricating thereof, and more particularly to a process for fabricating a pattern formed of opaque and transparent portions on an inner surface of a capillary device.

INTRODUCTION

Flow cytometry is a widely used technique in research centers and diagnostic labs for the detection and counting of cells. Using different labelling agents, one can selectively determine the cell type or some intrinsic parameter of cells. Recent advances in the development of biosensors based on luminescence [1,2,3,4] able to transduce the presence of biomolecules or biological events call for particle counting techniques with enhanced sensitivity, since the response of classical flow cytometers decrease as a function of emitter size.

Fluorescent marker-based detection offers many advantages over scattering-based detection, including its high sensitivity and the versatility provided by the large variety of functionalized fluorescent dyes commercially available across the electromagnetic spectrum (from the near UV to the near IR) that can be spectrally isolated from the scattered excitation light background. Consequently, light-emitting particles such as fluorescent nanoparticles or quantum dots have become markers of choice because of their high luminosity, photostability [5] and ease of surface functionalization [6, 7]. In recent years, considerable effort has been put into the development of fluorescent particles for applications in biosciences such as protein tracking [8], cellular imaging [9] and transduction of DNA hybridization [4, 10].

Many particle counting techniques have been developed over time to keep pace with this growing field of study and to widen the range of applications of fluorescent particles. Some of those techniques operate on solid and fixed samples, such as fluorescence microscopy which is widely used for imaging purposes [9]. Many other detection strategies have been developed to count particles dispersed in a liquid sample, with flow cytometry being probably the most widely used technique for the detection and quantification of fluorescent particles, mainly due to its high throughput [11-13]. Lately, flow cytometry schemes using microfluidic devices have been developed in an effort to make this technique more affordable, more compact and deployable at point-of-care settings [10].

Classical flow cytometry uses a highly focused excitation beam to probe a small (<1 mm$^3$) volume inside a capillary. High excitation power densities and detection schemes requiring precise optical alignment are often needed to achieve sufficient signal-to-noise ratios (SNR) in order to detect the fluorescence emitted from an individual particle during the short transit time through the probed volume.

Kiesel, P., et al., [14,15] describe an optical detection technique for a flow cytometer, which delivers high signal-to-noise discrimination without precision optics to enable a flow cytometer that can combine high performance, robustness, compactness, low cost, and ease of use. The technique was termed "spatially modulated emission" and generates a time-dependent signal as a continuously fluorescing bioparticle traverses a predefined pattern for optical transmission. Correlating the detected signal with the known pattern achieves high discrimination of the particle signal from background noise. The technique is demonstrated with measurements of fluorescent beads flowing through a microfluidic chip. This spatial signal encoding scheme has been applied to cell sorting techniques in microfluidic systems [16]

The present disclosure refers to a number of documents, the contents of which are herein incorporated by reference in their entirety.

SUMMARY

In an embodiment, the present disclosure relates to a process for fabricating a patterned capillary device, the process comprising thiolating an inner surface of the capillary; exposing a plurality of segments of the capillary to a source of radiation, the plurality of exposed segments defining a pattern; and flowing a solution comprising gold seeds though the capillary, the seeds adhering to non-exposed segments of the inner surface.

In a further embodiment, the present disclosure relates to a patterned capillary device comprising a wall having an outer surface and an inner surface, the wall defining a fluidic channel; and a substantially opaque film covering the inner surface of the wall, the opaque film comprising a plurality of substantially transparent segments defining a pattern.

In a further embodiment, the present disclosure relates to a flow cytometry kit comprising a radiation source for emitting a light beam having an elongated footprint; and a first mount including:

first opposed sidewalls defining opposite first openings for receiving a capillary device; a second sidewall perpendicular to the first opposed sidewalls and defining a second opening for mounting the radiation source and for receiving the light beam to be emitted onto the received capillary device.

The foregoing and other advantages and features of the present disclosure will become more apparent upon reading of the following non-restrictive description of illustrative embodiments thereof, given by way of example only with reference to the accompanying drawings/figures.

DRAWINGS

For a better understanding of the embodiments described herein and to show more clearly how they may be carried into effect, reference will now be made, by way of example only, to the accompanying drawings which show at least one exemplary embodiment, and in which:

FIG. 1 illustrates a front elevation view of an exemplary capillary device in accordance with the present disclosure;

FIG. 2 illustrates a side elevation view of the exemplary capillary device in accordance with the present disclosure;

FIG. 3 illustrates a perspective view of an exemplary substrate in an intermediate state according to an exemplary process for fabricating a patterned substrate in accordance with the present disclosure;

FIG. 4a illustrates a perspective view of an exemplary substrate surface in an intermediate state according to an exemplary process for fabricating a patterned substrate in accordance with the present disclosure;

DESCRIPTION OF VARIOUS EMBODIMENTS

Figure 4B:
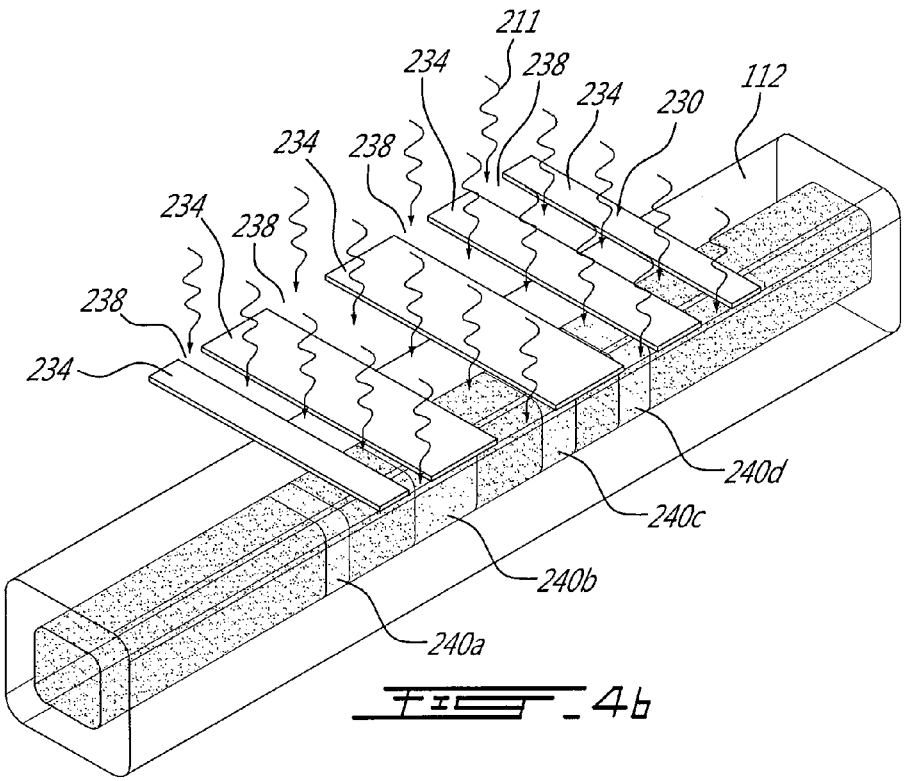
FIG. 4b illustrates a perspective view of an exemplary capillary device being exposed to a light source according to an example of the present disclosure.

It will be appreciated that, for simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way but rather as merely describing the implementation of the various embodiments described herein.

The word "a" or "an" when used in conjunction with the term "comprising" in the claims and/or the specification may mean "one", but it is also consistent with the meaning of "one or more", "at least one", and "one or more than one" unless the content clearly dictates otherwise. Similarly, the word "another" may mean at least a second or more unless the content clearly dictates otherwise.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this specification and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±1% of the modified term if this deviation would not negate the meaning of the word it modifies.

As used herein, the term "opaque" and variants thereof refer to layers having less than 25% total luminous transmittance. Opaque layers according to the disclosure typically have a total luminous transmittance of less than 20%, or less than 15%, or less than 10%.

As used herein, the term "transparent" and variants thereof refer to layers having greater than 75% total luminous transmittance. Transparent layers according to the disclosure typically have a total luminous transmittance of greater than 80%, or greater than 85%, or greater than 90%.

Referring now to FIGS. 1 and 2, therein illustrated are a front elevation and a side elevation view respectively of an untreated capillary device 100. The untreated capillary device 100 comprises a wall 104 having an outer surface 108 and an inner surface 112. The wall 104 extends the length of the capillary device 100 and defines a longitudinal fluidic channel 116. The capillary device 100 provides for a liquid to flow through the fluidic channel 116. In an embodiment of the present disclosure, the untreated capillary device 100 is a square capillary tube. In a further embodiment of the present disclosure, the fluidic channel 116 has a width of about 50 μm to 100 μm, while the total width of the untreated capillary device 100 including the wall 104 has a width of about 300 μm. In further embodiments of the present disclosure, the fluidic channel 116 has a width of up to 1 mm. In yet a further embodiment of the present disclosure, the wall 104 is formed of silica. The outer surface 108 of the wall 104 can be coated with a polyamide layer.

In the untreated state, the wall 104 of the capillary device 100 is substantially transparent to allow passage of light there through. For example, the untreated capillary device 100 has a total transmittance of at least 75%. In an embodiment of the present disclosure, the untreated capillary device 100 has a total transmittance of about 100%.

Referring now to FIG. 3, therein illustrated is a perspective view of a substrate 200. In an embodiment of the present disclosure, substrate 200 can be any type of glass or silica substrate. In a further embodiment of the present disclosure, substrate 200 can be any type of plastic substrate. According to one exemplary embodiment, the substrate 200 can represent a portion of wall 104 of an untreated capillary device 100.

According to an exemplary process for fabricating a patterned substrate, a surface 204 of the substrate 200 is functionalized to cover the surface 204 with a plurality of hydroxide groups. In an embodiment of the present disclosure, surface 204 represents the inner surface 112 of the untreated capillary device 100. According to an exemplary process for fabricating a patterned substrate, the inner surface 112 of capillary device 100 is treated with a piranha solution resulting in the functionalization of the inner surface 112. Treatment using a piranha solution results in the hydroxylation of the inner surface 112 of the capillary device 100. The piranha solution is typically allowed to flow through the fluidic channel 116 of the capillary device 100. In an embodiment of the present disclosure a diluted (50%) piranha solution is used. The inner surface 112 is subsequently treated with a $NH_4OH:H_2O_2:H_2O$ (1:1:1) solution. In a further embodiment of the present disclosure, the inner surface 112 is washed with water prior to being treated with the piranha solution. In a further embodiment of the present disclosure, the $NH_4OH:H_2O_2:H_2O$ (1:1:1) solution is allowed to flow through the fluidic channel 116 of the capillary device 100 for about 5 minutes at a rate of about 50 uL/min. In yet a further embodiment of the present disclosure, the fluidic channel 116 is rinsed prior to treatment with the $NH_4OH:H_2O_2:H_2O$ (1:1:1) solution. It will be understood that the above-described treatment results in substantially the entire inner surface 112 of the capillary device 100 being hydroxylated. For example, in the case of a square capillary device wherein the microfluidic channel 116 has a square cross-section defined by four sides of the inner surface 112 of the wall 104, each of the four sides of the inner surface 112 are hydroxylated following the functionalization.

Continuing with FIG. 3, in accordance with a process for fabricating the patterned substrate, the surface 204 of the substrate 200 is thiolated. In an embodiment, thiolation is carried out by flowing a solution comprising a thiolating agent over the surface 204 of substrate 200. In an embodiment of the present specification, the thiolating agent is 3-mercaptopropyltrimethoxysilane (MPTMS) 208. It is to be understood that the present disclosure is not limited to MPTMS as other thiolating agents will become readily apparent to the skilled artisan.

According to an exemplary process for the fabrication of a patterned substrate, a thiolating agent is allowed to flow through the fluidic channel 116 of the capillary device 100 for a period of time sufficient to effect the thiolation of the inner surface 112 of the capillary device 100. In an embodiment of the present disclosure, a 1% (V/V) solution of MPTMS in ethanol is allowed to flow through the fluidic channel 116 of the capillary device 100 at a rate of about 1 mL/h for approximately 12-15 hours. It will be understood that the above-described treatment results in substantially the entire inner surface 112 of the capillary device 100 being thiolated.

Referring now to FIG. 4a, therein illustrated is a perspective view of an exemplary substrate 200 comprising a thiolated surface 204 in an intermediate state being subjected to radiation 211 using a spatially patterned mask 230. In an embodiment of the present disclosure, the spatially patterned mask 230 comprises a plurality of opaque portions 234 that substantially block the passage of radiation and a plurality of transparent portions or gaps 238 that allow the passage of radiation there through. In an embodiment, a spatially patterned mask is positioned over the thiolated surface which is subsequently subjected to U.V. radiation. The spatially patterned mask results in parts of the thiolated surface 204 being subjected to radiation whereas other parts are substantially shielded from the radiation. As illustrated in FIG. 4a, subareas 216 and 218 of the thiolated surface 204 are exposed to the source of radiation 211 while subareas 220, 222 and 224 are left substantially unexposed. In an embodiment of the present disclosure, the radiation source is a U.V. light source which generates ozone in the exposed subareas 216, 218 of the thiolated surface 204. The ozone subsequently reacts with the thiol groups to produce sulfonate groups [18] or the corresponding sulfonic acid. According to various exemplary embodiments of the present disclosure, the radiation source 211 can be a pulsed U.V. laser beam. In a non-limiting example of the present disclosure, the pulsed laser beam has a wavelength of about 308 nm; has an energy of about 120 mJ, and has a pulsed frequency of about 100 Hz. In yet a further embodiment of the present disclosure, the laser beam has beam footprint incident on the thiolated surface 204 corresponding to the exposed subareas 216 and 218. Alternatively, the laser beam can be a focused beam that is swept over the exposed subareas 216 and 218 of the thiolated surface 204.

In an exemplary embodiment of the present disclosure, the sizes of the transparent portions/gaps 238 of the mask 230 are pseudorandom or random. For example, the gaps can be shaped as a plurality of parallel lines having pseudorandom or random widths to define a barcode-like pattern. Accordingly, the exposed subareas 216 and 218 of the thiolated surface 204 will also define a corresponding barcode-like pattern. While the barcode-like pattern is essentially one-dimensional, it will be understood that the transparent portions/gaps 238 of the mask 230 can also define a two-dimensional pattern and form exposed subareas having a corresponding two-dimensional pattern. According to various exemplary embodiments of the present disclosure, the mask 230 is a microfabricated mask. For example, the mask 230 can be a transmission-microscopy transmission (TEM) grid. The width of the transparent portions/gaps 238 can be between 10 μm and 1 mm.

Referring now to FIG. 4b, and in accordance with an exemplary process for fabricating a patterned substrate on an inner surface of a capillary device 100, the radiation source 211 is external to the capillary device 100 and is directed towards the thiolated inner surface 112 of the capillary device 100.

Figure 4C:
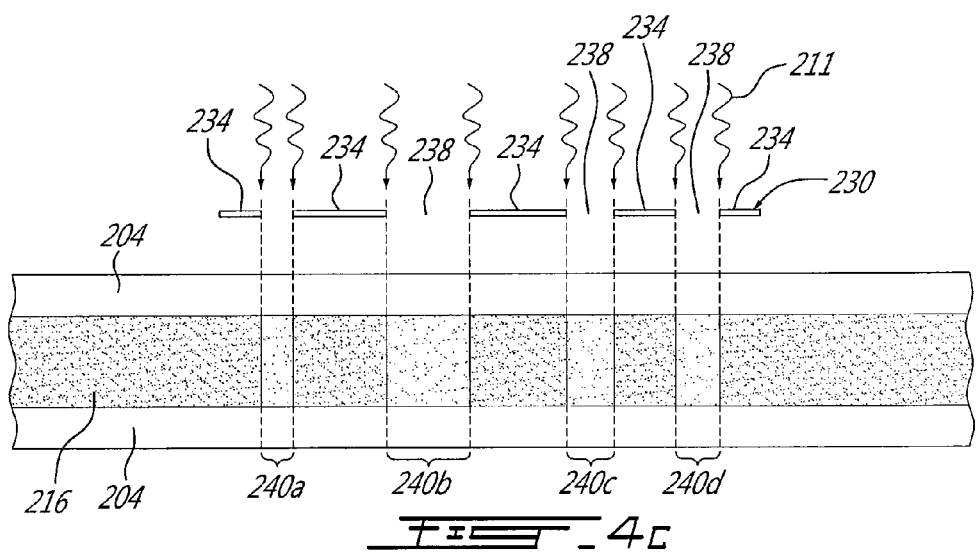
FIG. 4c illustrates a close up view of a portion of the exemplary capillary device being exposed to a light source according to an example of the present disclosure.

Referring now to FIG. 4c, a plurality of sub-segments 240a, 240b, 240c, and 240d of the capillary device 100 are exposed to a radiation source 211. Remaining portions of the capillary device 100 are left unexposed. It will be understood that since the wall 104 of the capillary device 100 is substantially transparent, light hitting one side of the wall 104 is transmitted through the microfluidic channel 116 to reach the opposing side of the wall 104. As a result, for each exposed sub-segment 240a, 240b, 240c, and 240d of the capillary device 100, there will be a substantially equivalent sub-segment on the opposite side of the microfluidic channel 116. In yet a further embodiment of the present disclosure, the pattern defined by the mask 230 is reproduced on substantially the entire inner circumference/surface of the microfluidic channel 116.

Figure 5:
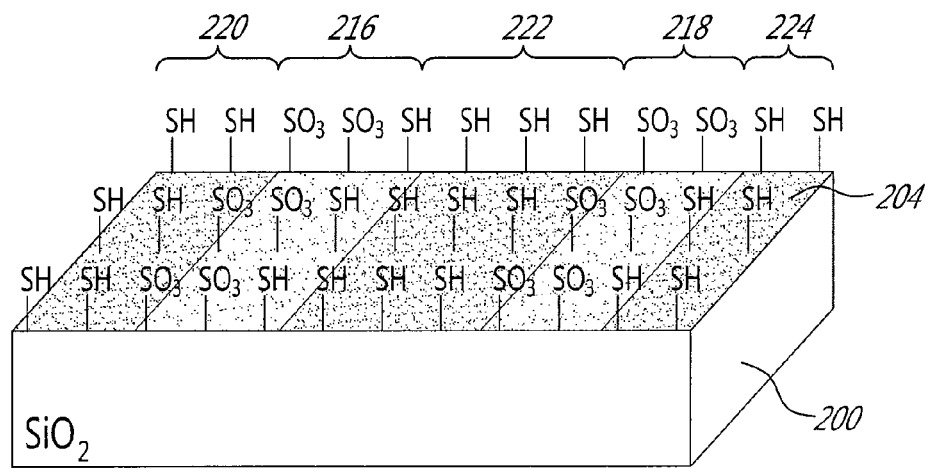
FIG. 5 illustrates a perspective view of an exemplary substrate in an intermediate state according to an exemplary process for fabricating a patterned substrate in accordance with the present disclosure.

Referring now to FIG. 5, therein illustrated is a perspective view of the substrate 200 in an intermediate state following exposure to the radiation source 211 in accordance with an exemplary process for fabricating a patterned substrate. It will be appreciated that subareas 216 and 218 of the thiolated surface 204 that were exposed to the radiation source 211 now comprise sulfonate groups or the corresponding sulfonic acid. It will be further appreciated that subareas 220, 222, and 224 of the thiolated surface 204 that were not exposed to the radiation source remain substantially unchanged and thus comprise thiol groups.

Figure 6:
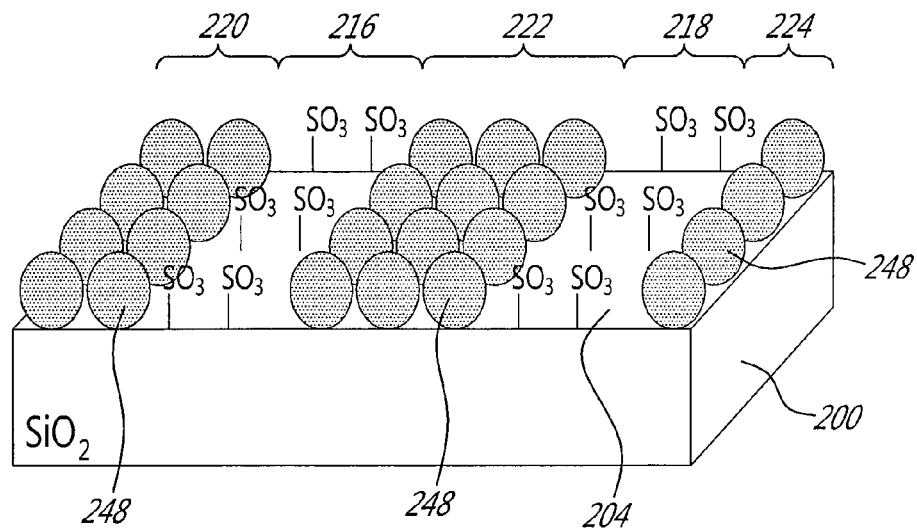
FIG. 6 illustrates a perspective view of an exemplary substrate in an intermediate state according to an exemplary process for fabricating a patterned substrate in accordance with the present disclosure.

Referring now to FIG. 6, therein illustrated is a perspective view of a patterned substrate comprising gold seeds 248. In accordance with an exemplary process for fabricating a patterned substrate, a gold seed solution is allowed to flow through the microfluidic channel 116. The gold seeds will interact with the thiol functionalities of subareas 220, 222, and 224 resulting in their adherence thereto. The gold seeds do not adhere to the sulfonate groups or the corresponding sulfonic acid of subareas 216 and 218. Circumferential portions of the inner surface 112 corresponding to the exposed sub-segments of the capillary device 100 are non-reactive, and accordingly these portions of the inner surface remain substantially free of gold seeds. In a particular embodiment of the present disclosure, the gold seed solution is allowed to flow through the fluidic channel 116 of the capillary device 100 over a period of time of about 3 hours at a flow rate of approximately 100 µL per hour. In accordance with a non-limiting example of the present disclosure, a mixture of a $H_2O_2$ solution and a $HAuCl_4$ solution is allowed to flow through the fluidic channel 116 of the capillary device 100. More specifically, a mixture of a $H_2O_2$ solution and $HAuCl_4$ solution is allowed to flow through the fluidic channel 116 of the capillary device 100 using two syringe pumps, each holding one of the two solutions. For example, the $HAuCl_4$ is a 0.02% $HAuCl_4$ solution and the $H_2O_2$ solution is a 10% solution. Both syringes are running at a flow rate of approximately 50 uL/min.

Figure 7:
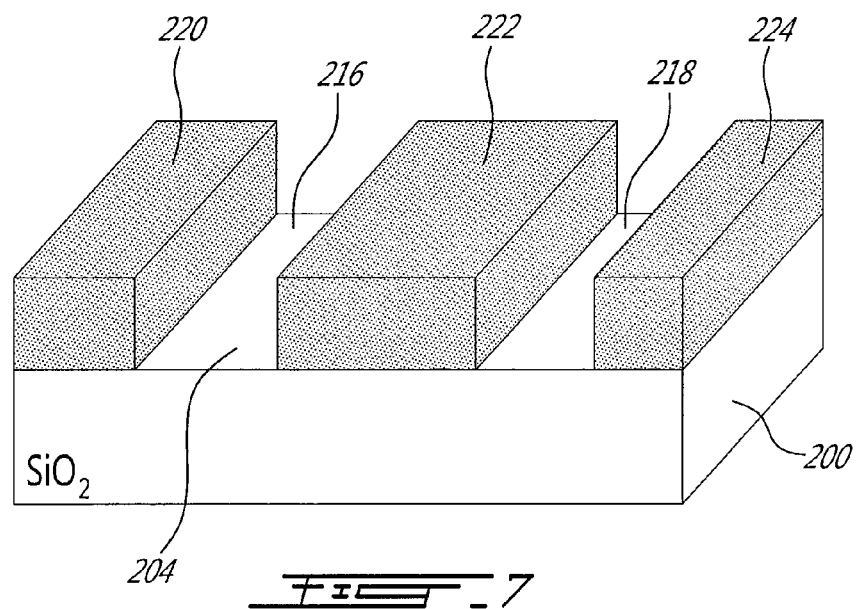
FIG. 7 illustrates a perspective view of an exemplary substrate comprising a patterned gold film in accordance with the present disclosure.

Referring now to FIG. 7, therein illustrated is a perspective view of a patterned substrate comprising a gold film. More specifically, subareas 220, 222 and 224 of the surface 204 are now covered by a gold film. Gold film covered subareas 220, 222, and 224 are substantially opaque and have a low light transmittance. Exposed subareas 216 and 218 are substantially free of gold film and are substantially transparent (high transmittance of light).

Figure 8:
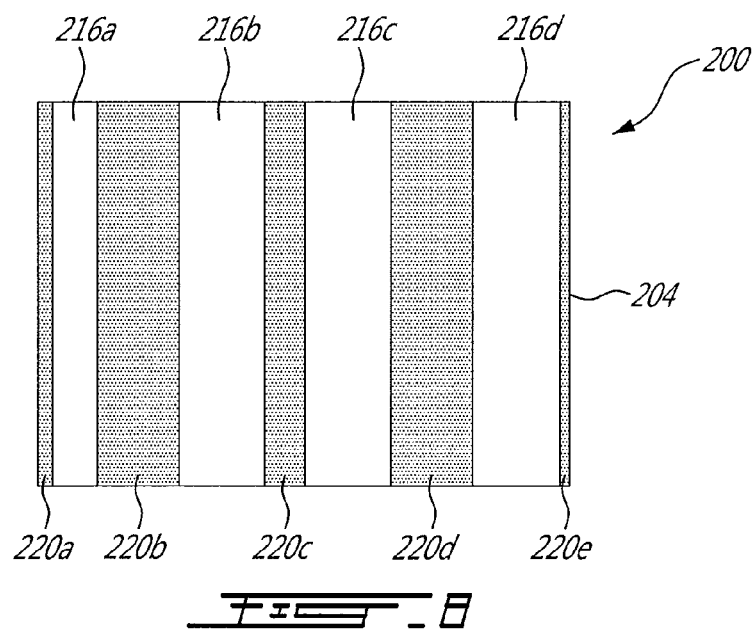
FIG. 8 illustrates a plan view of an exemplary substrate comprising a patterned gold film in accordance with the present disclosure.

Referring now to FIG. 8, therein illustrated is a plan view of a surface 204 of an exemplary patterned substrate. Subareas 220a, 220b, 220c, 220d, and 220e are comprise a gold film and are substantially opaque. These subareas correspond to the thiolated subareas of the surface 204 that were unexposed to the radiation source 211. Subareas 216a, 216b, 216c, and 216d are substantially free of gold film and are substantially transparent. These subareas correspond to thiolated subareas of the surface 204 that were exposed to the radiation source 211 and rendered non-reactive to the gold seeds 248. It will be appreciated that the opaque subareas 220 and transparent subareas 216 are in the shape of parallel lines of random or pseudorandom widths and define a barcode-like pattern.

Figure 9:
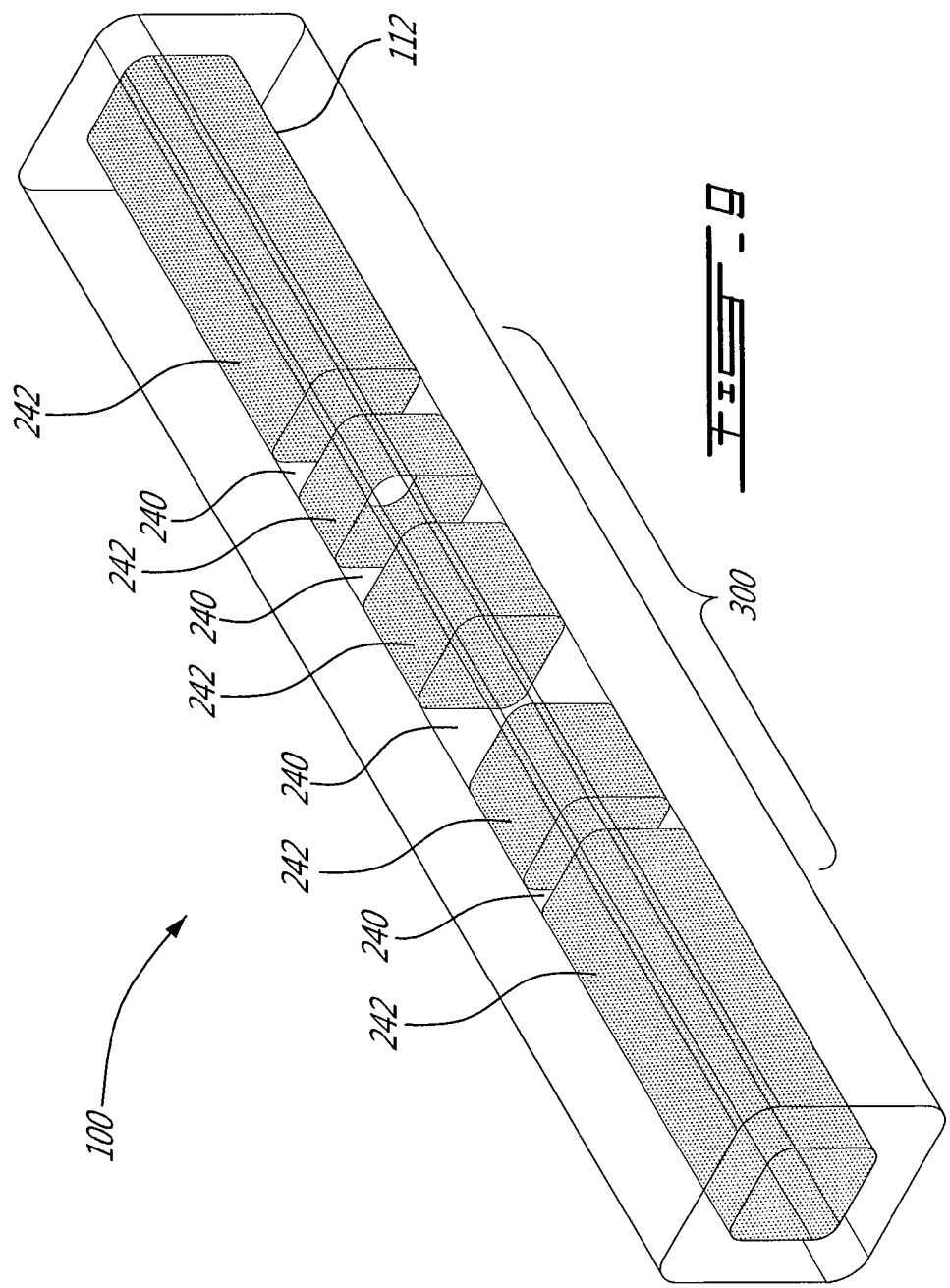
FIG. 9 illustrates a side elevation view of an exemplary patterned capillary device fabricated according to an exemplary process of the present disclosure.

Referring now to FIG. 9, therein illustrated is a side elevation view of an exemplary patterned capillary device 100. A patterned portion 300 on an inner surface 112 of a segment of the capillary device 100 defines opaque and transparent surfaces. Shaded areas 242 correspond to portions of the inner surface 112 that were unexposed to the radiation source 211. Clear areas 240 correspond to portions of the inner surface 112 that were exposed to the radiation source 211. It will be appreciated that each opaque (shaded) or clear portion extends circumferentially about the inner surface 112 of the capillary device 100. It will be further appreciated that in the longitudinal direction of the inner surface 112, the opaque portions 242 and the clear portions 240 define a barcode-like pattern, wherein the opaque 242 and clear portions 240 have pseudorandom or random widths.

According to a flow cytometry method using the patterned capillary device 100 as disclosed herein, an analyte is allowed to flow through the patterned fluidic channel 116. In an embodiment of the present disclosure, the analyte is fluorescent and emits a measurable light signal when excited. In a further embodiment of the present disclosure, an excitation source is projected onto the patterned portion 300 of the capillary device 100 to excite the analyte as it flows through the patterned portion. In a non-limiting example of the present disclosure, the analyte is one or more calibration beads.

Due to the opaque gold film pattern deposited on the inner surface 112 of the capillary device 100, as the excited analyte flows through the microfluidic channel 116, fluorescence emitted by the analyte will only be perceivable when the analyte transitions within a transparent portion 240 of the capillary device 100. Within the opaque portions 242 of the capillary device 100, fluorescence emitted by the analyte is blocked. The measured fluorescent signal is thus a time-varying signal. The time-varying signal depends upon one or more of the amplitude of the fluorescence emitted by the analyte, the speed of travel of the analyte through the microfluidic channel 116 of the capillary device 100, and the widths of opaque portions 242 and clear portions 240 defining the patterned portion 300. Accordingly, if the widths of opaque portions 242 and transparent 240 are established, a theoretical fluorescent signal can be calculated. The theoretical signal can then be cross-correlated with the measured fluorescent signal of the analyte in order to better resolve the measured fluorescent signal of the analyte. It has been surprisingly discovered that a pseudorandom or random signal improves the correlation of the theoretical signal and the measured signal. Such a flow cytometry method resembles the "spatially modulated emission" method.

Advantageously, the gold film forming the opaque portions 242 of the pattern 300 deposited on the inner surface 112 of the capillary device 100 are protected from physical wear or damage. Unlike a pattern formed on an outer surface, the pattern formed on the inner surface will retain its barcode-like pattern for longer periods of time. Moreover, since the pattern is deposited on the inner surface 112 of the fluidic channel 116, it is closer to the analyte and thus provides an improved fluorescent signal. For example, fluorescent light emitted from the analyte will undergo less scattering before being transmitted through the clear portions 240 of inner surface 112. Advantageously, the opaque portions 242 and the transparent portions 240 of the inner surface 112 extend circumferentially around the inner surface 112 of the capillary device 100. As a result, the microfluidic channel 116 can be viewed at various angles around the capillary device 100. This enables the placement of several optical channels around the capillary device 100 for easy multiplex detection.

Figure 10:
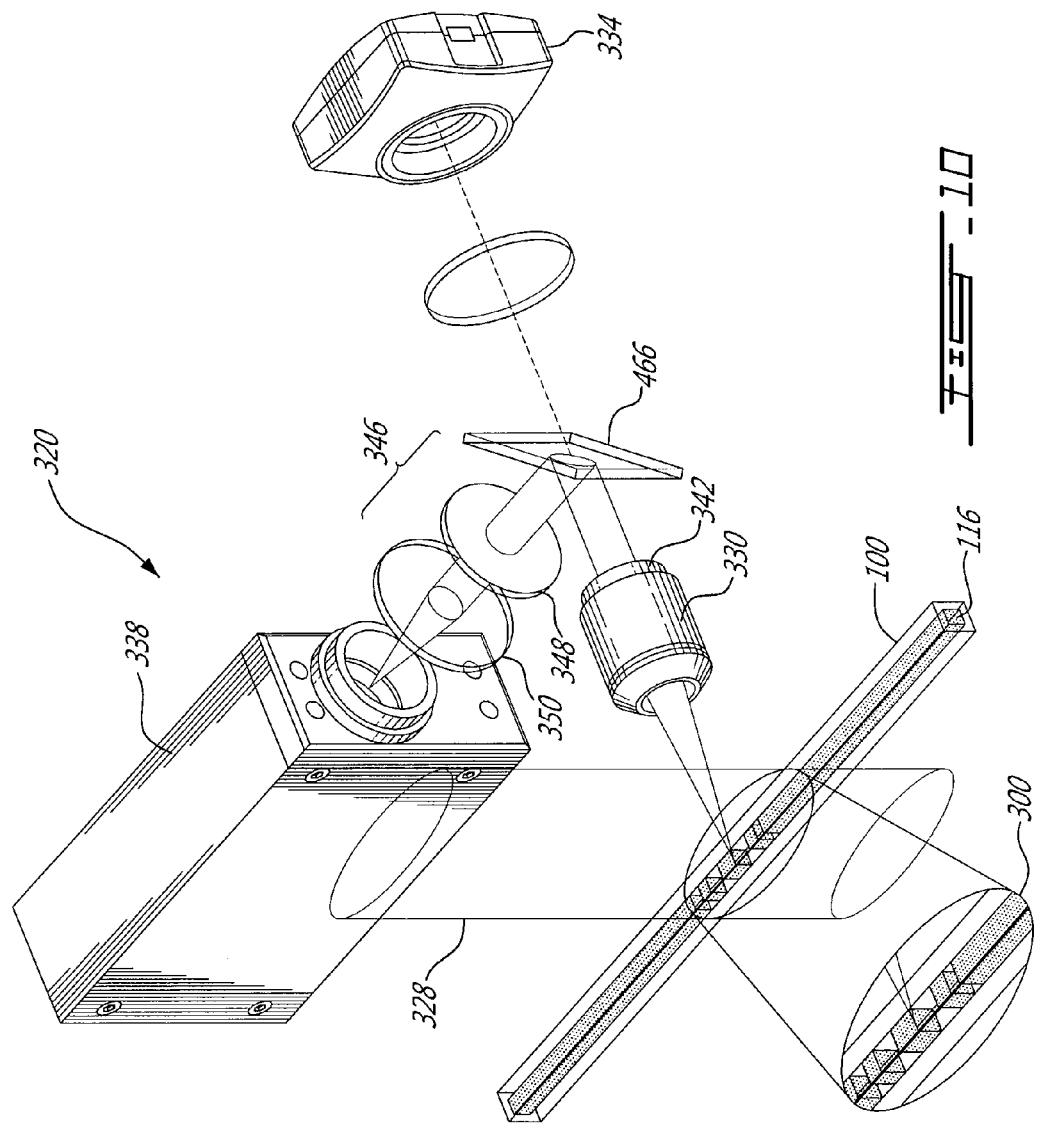
FIG. 10 illustrates a perspective view of an arrangement of components of an exemplary flow cytometry apparatus in accordance with an embodiment of the present disclosure.

Referring now to FIG. 10, therein illustrated is a perspective view of an arrangement of components of an exemplary flow cytometry apparatus 320 for analysis of an analyte using the patterned capillary device 100. It will be understood that the components of the flow cytometry apparatus 320 can be provided as a kit and assembled on-site for flow cytometry analysis. The flow cytometry apparatus can include a light source to be aligned with the patterned portion 300 deposited in the patterned capillary device 100. The radiation source can emit an excitation beam 328 at the patterned portion 300 of the patterned capillary device 100 to excite the analyte flowing through the fluidic channel 116. In an embodiment of the present disclosure, the excitation beam 328 has an incident angle that is substantially perpendicular with the patterned portion 300 of the capillary device 100. The radiation source can be further adjustable to emit an excitation beam 328 at various frequencies depending on the type of analyte to be excited.

According to various exemplary embodiments of the present disclosure, the radiation source includes a laser source, a laser beam expander, a cleanup filter and an elongating lens. A laser beam emitted from the laser source is first expanded by the laser beam expander. In an embodiment of the present disclosure, the laser source is a 488 nm laser diode source which is expanded to approximately 6 mm in diameter by the be beam expander. The expanded beam is passed through a cleanup filter in order to filter out any unwanted light frequencies and to retain only those frequencies of interest. The elongating lens focuses the cleaned up laser beam and projects an elongated excitation beam 316 onto the patterned portion 300 of the patterned capillary device 100. In a particular embodiment of the present disclosure, the elongating lens is a plano-convex cylindrical lens. The elongated beam can have a footprint with dimensions of about 2400 μm×200 μm, which can substantially correspond to the patterned portion 300 of the patterned particular device 100. As shown in FIG. 10, the elongated excitation beam 316 is projected onto the patterned portion 300 of the patterned capillary device 100.

The flow cytometry apparatus 320 further includes a magnifying objective 330 that is positioned to magnify the patterned portion 300 of the patterned capillary device 100. In a non-limiting embodiment of the present disclosure, the magnifying objective 330 is a 10× microscope objective. An image capturing device 334 or a photomultiplier 338 can be aligned with the viewing end 342 of a microscope objective 330 in order to measure the light emitted from the patterned portion 300 of the capillary device 100. In a non-limiting embodiment of the present disclosure, the image capturing device 334 can be CCD or CMOS camera, which can be further used for alignment or optimization purposes. The photomultiplier module 338 receives a light signal (photons) transmitted from the viewing end 342 of the magnifying objective 330 and counts the amount of particles (photons) in the light signal. For example a filter system 346 can be positioned between the magnifying objective 330 and the photomultiplier 338 in order to filter the light signal prior to reaching the photomultiplier 338. In a non-limiting embodiment of the present disclosure, the filter system 346 is formed of a notch filter 348 and a bandpass filter 350 that matches the frequency of interest.

Figure 11:
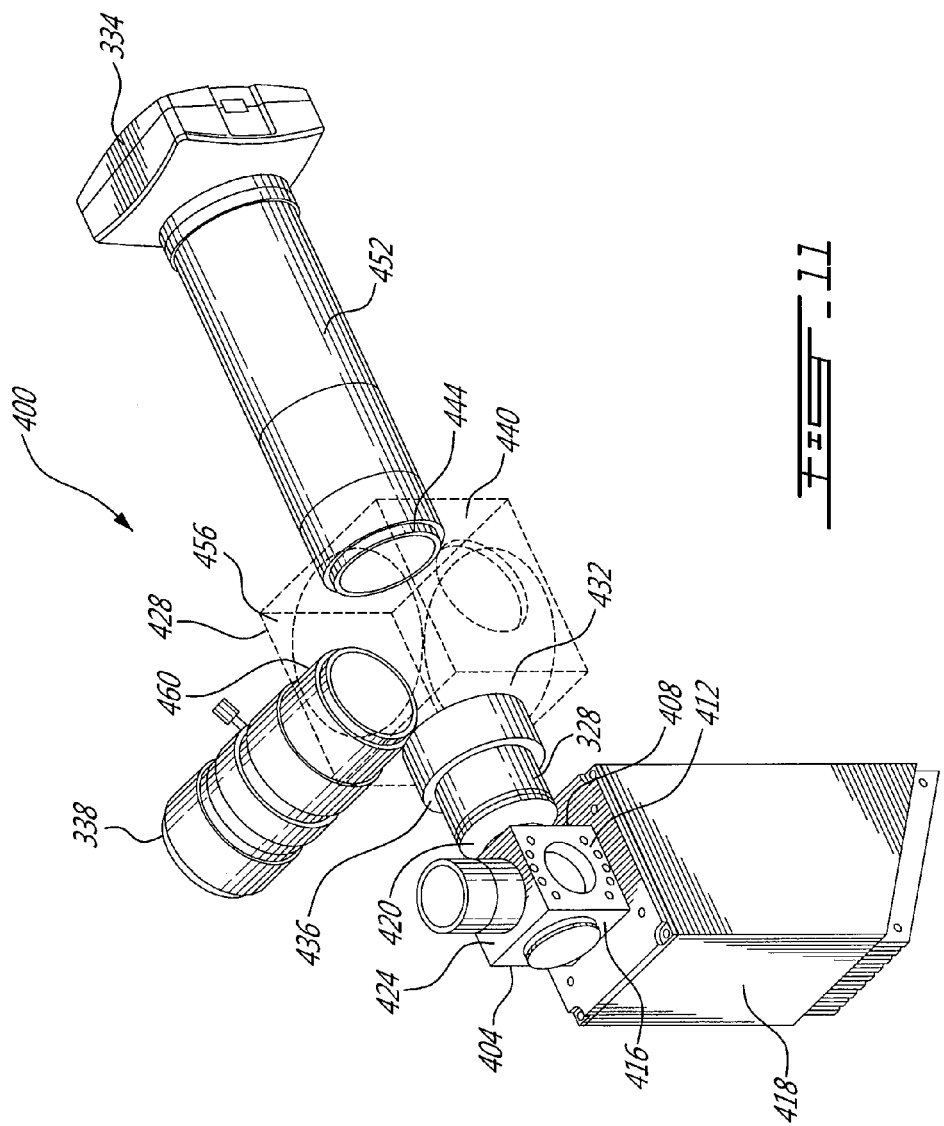
FIG. 11 illustrates a perspective view of an exemplary flow cytometry apparatus assembled from components of an exemplary kit for low cytometry detection in accordance with the present disclosure.

Referring now to FIG. 11, therein illustrated is a perspective view of a flow cytometry apparatus that has been assembled from the components of an exemplary kit 400. The flow cytometry kit 400 includes a first mount 404 having first opposed sidewalls 408 defining opposing first openings 412. The openings 412 are appropriately shaped such that a patterned capillary device 100 can project through the openings 412 and be supported by the first mount 404. The patterned capillary device 100 can be positioned such that its patterned portion 300 is located within the mount 404. The first mount has a second sidewall 416 perpendicular to the first sidewalls 408. The second sidewall 416 defines a second opening for mounting a light source 418. When both the light source 418 and the capillary device 100 are mounted onto the first mount 404, light beam 328 from the light source 418 is incident upon the patterned portion 300 of the patterned capillary device 100.

The first mount 404 of kit 400 further includes a third sidewall 420 defining a third opening 424 for mounting the enlarging end of the microscope objective 320. The enlarging end of the microscope objective 320 captures light being emitting from the capillary device 100 through the transparent portions of the patterned portion 300. In an embodiment of the present disclosure, the light being emitting from the capillary device 100 is from an excited analyte flowing through the fluidic channel 116 of the capillary device 100.

The kit 400 further includes a second mount 428, which has a first sidewall 432 defining a first opening 436. The second mount 428 further includes a second sidewall 440 opposite the first sidewall 432 and defining a second opening 444. The viewing end of the microscope objective can be mounted onto the first opening 436 of the second mount 428. Either one of a photomultiplier 338 or an imaging device 334 can be mounted onto the second opening 444 opposite the first opening 436. Mounting of the imaging device 324 or photomultiplier 328 onto the second opening 444 allows an image on the viewing end of the magnifying objective to be captured. In an embodiment of the present disclosure, the photomultiplier 338 or imaging device 334 can be mounted onto the second mount via a hollow tube 452.

According to various exemplary embodiments of the present disclosure, the second mount 432 further includes a third sidewall 456 perpendicular to the first sidewall 432 and second sidewall 440. When one of the imaging device 334 or photomultiplier 338 is mounted onto the second opening 444 of the second sidewall 440, the other device can be mounted onto the third opening 460 defined by third sidewall 456. It will be appreciated that the other device is mounted perpendicularly to the magnifying objective 328. A mirror 466 can be further mounted within the body of the second mount 432 to reflect light emitted from the viewing end of the magnifying objective 328 towards the photomultiplier.

EXPERIMENTAL

Unless described otherwise, chemicals were generally used as received without further purification. Gold chloride hydrate ($HAuCl_4 \cdot H_2O$, 99.9985%) was purchased from Strem Chemicals; hydrogen peroxide ($H_2O_2$, 30% w/w) was purchased from BDH; ammonium hydroxide ($NH_4OH$, 28-30%), sodium borohydride ($NaBH_4$, 99%), (3-mercaptopropyl)trimethoxysilane (MPTMS, 95%) and sodium citrate tribasic dihydrate (≥99%) where purchased from Sigma-Aldrich.

A glass capillary was washed and subsequently treated by first allowing a diluted (50%) piranha solution to flow there through followed by a $NH_4OH:H_2O_2:H_2O$ (1:1:1) solution for about 5 minutes at 50 μl/min. Rinsing of the capillary with water or ethanol between each preparation step was carried out to prevent unwanted side reactions within the capillary. The capillary inner surface was subsequently thiolated using a 1% (V/V) solution of MPTMS in ethanol (overnight flow at a rate of 1 mL/h).

After rinsing, the capillary is dried using a nitrogen or compressed air flow. The capillary is then exposed to a UV pulsed laser beam (308 nm, 120 mJ, 100 Hz) for about 60 seconds while using a microfabricated mask (KJ Laser Micromachining, Toronto, Canada) featuring the desired barcode pattern. The ozone generated by the UV light in the regions not exposed by the mask oxidizes the thiol groups into their corresponding sulfonate groups or the corresponding sulfonic acid. Thus, a latent print of the pattern is formed by the sulfonate moieties on the inside walls of the capillary.

Gold seeds are prepared based on [17]. Gold seeds are subsequently prepared using a 1% trisodium citrate solution (1 mL) and a 0.01% $HAuCl_4$ solution (100 mL). The citrate solution is added to a 0.01% $HAuCl_4$ solution (100 mL) under vigorous stirring. A 0.11% $NaBH_4$ in a 1% solution of trisodium citrate solution (1 mL) is added, and the solution is kept under agitation for an additional 5 minutes. At this point, the gold seed solution can be used immediately without further modification or stored in a refrigerator for later use. To complete the gold plating reaction, the seed solution is allowed to flow through the capillary for about 3 hours at 100 µL/h. The gold seeds adhere to the thiolated regions of the capillary inner wall, which correspond to the opaque zones of the mask.

Figure 12:
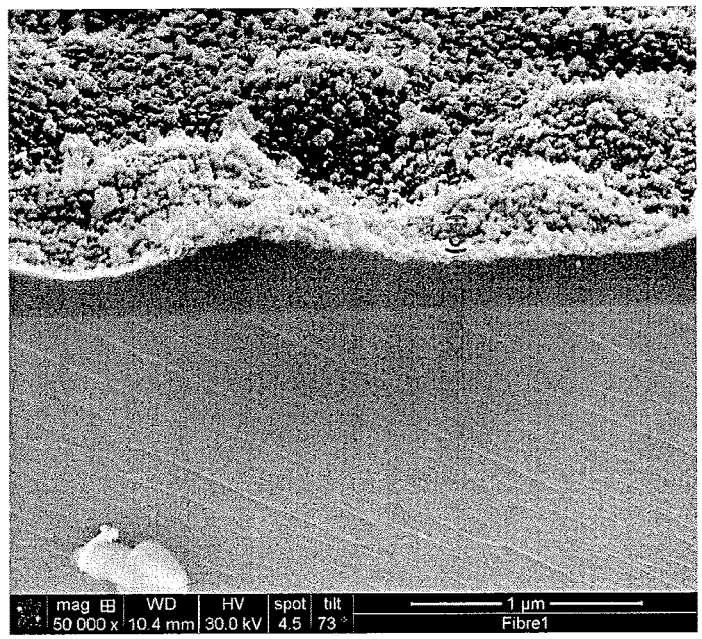
FIG. 12 illustrates a scanning electron microphotograph (SEM) of a gold film fabricated according to an exemplary experimental process of the present disclosure.
Figure 13:
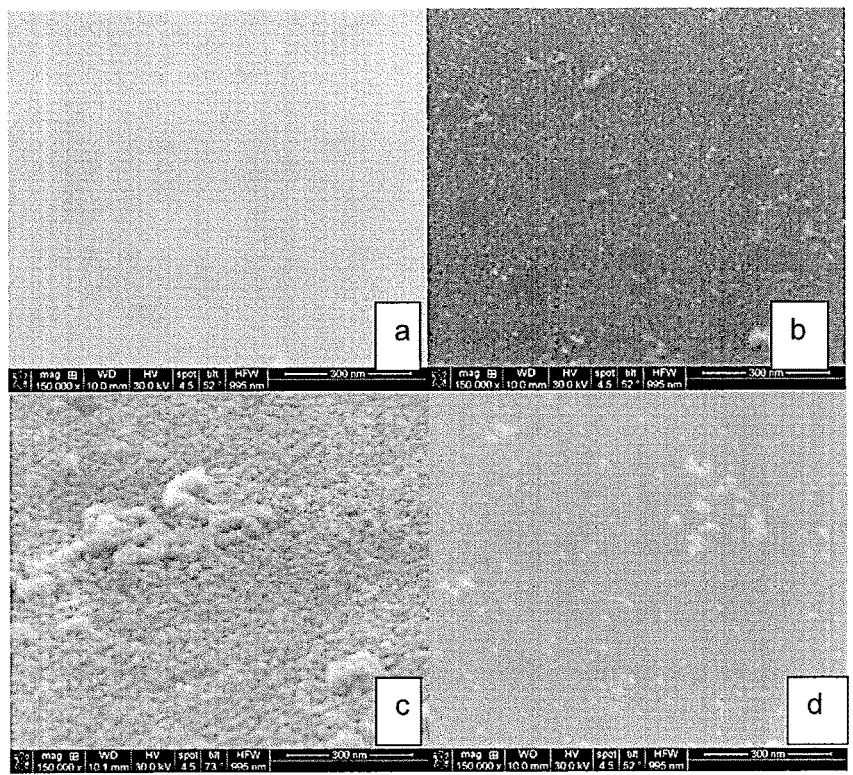
FIG. 13 illustrates SEM images of the capillary inner surface at various intermediate states of the exemplary experimental process in accordance with the present disclosure.

The last step consists in growing a gold film from the seeds adhering to the thiol functions by the reduction of a $HAuCl_4$ solution in the capillary. This is accomplished by mixing a 10% solution of $H_2O_2$ and a 0.02% solution of $HAuCl_4$ in the capillary using two syringe pumps running at 50 µL/min. The seeds grafted onto the surface will act as nucleation sites and the gold film will grow preferentially on the regions of the capillary that were shielded from ultraviolet (UV) light during exposure, leaving the exposed regions mostly free of gold. FIG. 12 illustrates a scanning electron microphotograph (SEM) of a gold film fabricated in accordance with an embodiment of the present disclosure. The method produces a gold coating of about 215 nm in thickness, which yields an optical density of >2 [19]. The coating covers the entire inner surface of the capillary except where the barcode pattern was imprinted and which constitutes the detection zone.

FIG. 13*a-d* illustrates SEM images of the capillary inner surface after: a) washing; b) seed grafting; and c) gold film growth. d) Illustrates a UV-exposed region after the gold reduction step, indicating that film growth only occurs in regions where seeds have been grafted, thus leaving the exposed areas clear. Isolated gold islands have been observed on the glass surface in UV-exposed regions, presumably due to the formation of gold seeds during the reduction step, which then adhere to the glass surface. This might lead to decreased transparency in the clear areas of the barcode, although a loss of optical mask contrast attributable to this has not been measured.

Figure 14:
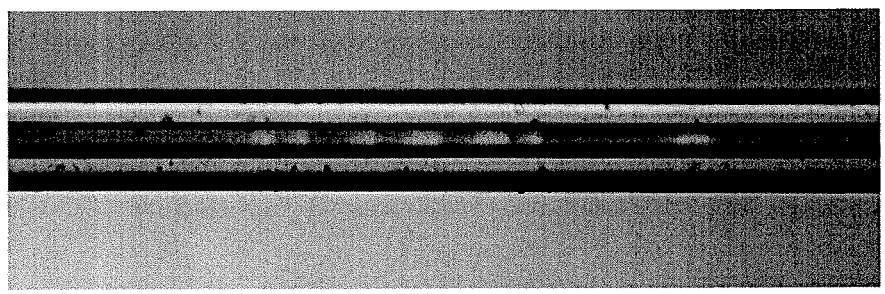
FIG. 14 illustrates an optical microphotograph of the resulting capillary fabricated according to an exemplary experimental process in accordance with the present disclosure.

FIG. 14 illustrates an optical microphotograph of a barcode design fabricated in accordance with an embodiment of the present disclosure. As shown, the barcode design has a smallest feature size of 40 µm and is sufficiently random to generate a sharp peak after autocorrelation. This particular geometry enables the detection of calibrations beads (Calibration kits 832 and 833, Bangs Laboratories) having diameters as small as 200 nm.

Figure 15:
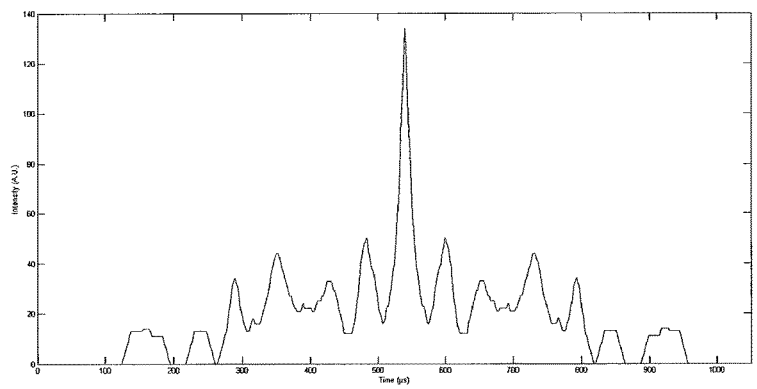
FIG. 15 illustrates a graph of a calculated auto-correlation for the barcoded pattern capillary of FIG. 14 in accordance with the present disclosure.

FIG. 15 illustrates a graph showing a calculated autocorrelation for the pseudo-random mask of FIG. 14.

Figure 16:
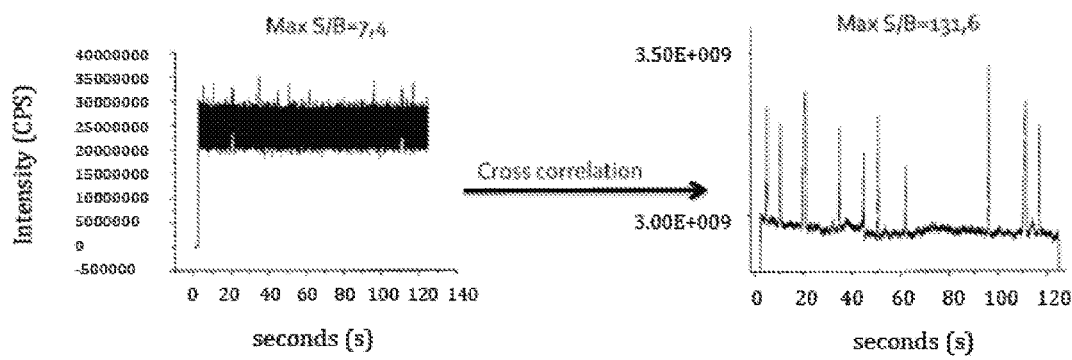
FIG. 16 illustrates measured raw and processed data of the light signal emitted through the capillary of FIG. 14 in accordance with the present disclosure.

FIG. 16 illustrates typical raw and processed data for a 120-second acquisition of 990-nm fluorescent calibration beads. Once the raw fluorescence time trace is processed with the cross-correlation algorithm, a baseline is fitted to the processed signal trace using a moving-window Savitzky-Golay algorithm and subtracted therefrom. Peaks over a predefined threshold of 2.5 times the standard deviation are marked as detected events.

Figure 17:
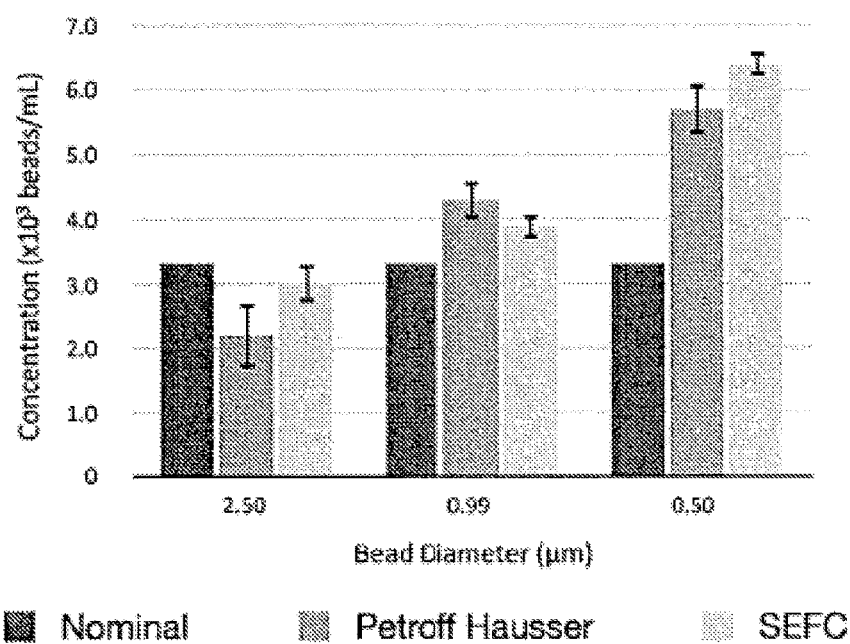
FIG. 17 illustrates a graph comparing the measurement obtained using the capillary of FIG. 14 versus other known methods in the art.

Suspensions of calibration beads having diameters of 0.5 µm, 0.99 µm and 2.5 µm respectively were flowed in the barcoded capillary (5 replicates per bead size) and their concentration was determined. As a reference, the concentration of the bead suspensions was also measured on a fluorescence microscope using a Petroff-Hausser counting chamber (Model 3900, Hausser Scientific) after washing and dilution. In order to make statistically valid measurements with the counting chamber, concentrated (stock) calibration bead suspensions were used for this counter method. These stock suspensions were then diluted prior to being measured by the flow cytometer. The results obtained with the two methods are presented in Table 1 and FIG. 17. The values obtained by the cytometer agree with those measured with the counting chamber, the difference being mainly attributable to errors that occurred during dilution and pipetting of the small stock solution volumes needed for analysis by the flow cytometer.

TABLE 1

Comparative results for the measurement of calibration bead suspensions by two independent techniques.

| | | Bead concentration ± standard deviation ($\times 10^3$ beads/mL) | |
|---|---|---|---|
| Bead diameter (µm) | Nominal | Petroff-Hausser | SEFC |
| 2.50 | 3.3 | 2.2 ± 0.5 | 3.0 ± 0.3 |
| 0.99 | 3.3 | 4.3 ± 0.3 | 3.9 ± 0.2 |
| 0.50 | 3.3 | 5.7 ± 0.4 | 6.4 ± 0.2 |

While the above description provides examples of the embodiments, it will be appreciated that some features and/or functions of the described embodiments are susceptible to modification without departing from the spirit and principles of operation of the described embodiments. Accordingly, what has been described above has been intended to be illustrative and non-limiting and it will be understood by persons skilled in the art that other variants and modifications may be made without departing from the scope of the invention as defined in the claims appended hereto.

REFERENCES

1. Jans, H., et al., *Dynamic light scattering as a powerful tool for gold nanoparticle bioconjugation and biomolecular binding studies.* Anal Chem, 2009. 81(22): p. 9425-32.
2. Graham, D., et al., *Control of enhanced Raman scattering using a DNA-based assembly process of dye-coded nanoparticles.* Nat Nanotechnol, 2008. 3(9): p. 548-51.
3. Pei, H., et al., *Designed diblock oligonucleotide for the synthesis of spatially isolated and highly hybridizable functionalization of DNA-gold nanoparticle nanoconjugates.* J Am Chem Soc, 2012. 134(29): p. 11876-9.
4. Brouard, D., et al., *Label-free biosensing based on multilayer fluorescent nanocomposites and a cationic polymeric transducer.* ACS Nano, 2011. 5(3): p. 1888-96.
5. Resch-Genger, U., et al., *Quantum dots versus organic dyes as fluorescent labels.* Nat Methods, 2008. 5(9): p. 763-75.
6. Liu, S., Z. Zhang, and M. Han, *Gram-scale synthesis and biofunctionalization of silica-coated silver nanoparticles for fast colorimetric DNA detection.* Anal Chem, 2005. 77(8): p. 2595-600.
7. Algar, W. R., et al., *The controlled display of biomolecules on nanoparticles: a challenge suited to bioorthogonal chemistry.* Bioconjug Chem, 2011. 22(5): p. 825-58.

8. You, C., et al., *Self-controlled monofunctionalization of quantum dots for multiplexed protein tracking in live cells.* Angew Chem Int Ed Engl, 2010. 49(24): p. 4108-12.
9. Geng, J., et al., *Conjugated polymer and gold nanoparticle co-loaded PLGA nanocomposites with eccentric internal nanostructure for dual-modal targeted cellular imaging.* Small, 2012. 8(15): p. 2421-9.
10. Tavares, A. J., et al., *On-chip transduction of nucleic acid hybridization using spatial profiles of immobilized quantum dots and fluorescence resonance energy transfer.* Anal Chem, 2012. 84(1): p. 312-9.
11. Smith, R. A. and T. D. Giorgio, *Quantitative measurement of multifunctional quantum dot binding to cellular targets using flow cytometry.* Cytometry A, 2009. 75(5): p. 465-74.
12. Muller, R. B., et al., *Detection of low level cryoglobulins by flow cytometry.* Cytometry A, 2012. 81(10): p. 883-7.
13. Yun, H., et al., *Simultaneous counting of two subsets of leukocytes using fluorescent silica nanoparticles in a sheathless microchip flow cytometer.* Lab Chip, 2010. 10(23): p. 3243-54.
14. Kiesel, P., et al., *Spatially modulated fluorescence emission from moving particles.* Applied Physics Letters, 2009. 94(4): p. 041107.
15. Kubby, J. A., et al., *Microfluidic-based detection platform for on-the-flow analyte characterization.* Proc. of SPIE, 2010. 7606: p. 760608.
16. Yu-Hwa Lo, C. H. R. C., Sung Hwan Cho, Frank Tsai, *fluidic flow cytometry device and particle sensing based on signal-encoding*, 2012: US20120079531.
17. Hu, J., et al., *Novel plating solution for electroless deposition of gold film onto glass surface.* Surface and Coatings Technology, 2008. 202(13): p. 2922-2926.
18. Huang, J., D. A. Dahlgren, and J. C. Hemminger, *Photopatterning of Self-Assembled Alkanethiolate Monolayers on Gold: A Simple Monolayer Photoresist Utilizing Aqueous Chemistry.* Langmuir, 1994. 10(3): p. 626-628.
19. Heavens, O. S., *Optical properties of thin films.* Vol. 1. 1960. 65.

The invention claimed is:

1. A process for fabricating a patterned capillary device, the process comprising:

thiolating an inner surface of the capillary;

exposing a plurality of segments of the capillary to a source of radiation, the plurality of exposed segments defining a pattern, wherein the pattern extends circumferentially around the inner surface of the capillary; and flowing a solution comprising gold seeds though the capillary, the seeds adhering to non-exposed segments of the inner surface.

2. The process of claim 1, further comprising growing a gold film from the seeds adhering to the non-exposed segments of the inner surface of the capillary device.

3. The process of claim 2, wherein the gold film-covered segments define opaque segments.

4. The process of claim 2, wherein the exposed segments are substantially free of the gold film.

5. The process of claim 4, wherein the exposed segments define transparent segments.

6. The process of claim 2 wherein growing the gold film comprises flowing a mixture of a $HAuCl_4$ solution and a $H_2O_2$ solution through the capillary.

7. The process of claim 1, wherein the exposed segments and the non-exposed segments define a barcode pattern on the inner surface of the capillary device.

8. The process of claim 7, wherein the barcode pattern is defined by a plurality of substantially parallel lines having random widths.

9. The process of claim 1, wherein thiolating the inner surface comprises the use of 3-mercaptopropyltrimethoxysilane.

10. The process of claim 1, wherein the radiation source comprises a UV light source.

11. The process of claim 10, wherein the UV light source comprises one or more of UV laser beams.

12. The process of claim 1, wherein exposing a plurality of segments of the capillary to a source of radiation comprises using a microfabricated mask defining a pattern.

13. The process of claim 12, wherein the microfabricated mask is a transmission-electron microscopy grid.

14. The process of claim 1, wherein the seed solution is flowed through the capillary for about 3 hours at about 100 µL per hour.

* * * * *

UNITED STATES PATENT AND TRADEMARK OFFICE
CERTIFICATE OF CORRECTION

PATENT NO. : 10,094,762 B2  
APPLICATION NO. : 13/905992  
DATED : October 9, 2018  
INVENTOR(S) : Boudreau et al.

Page 1 of 1

It is certified that error appears in the above-identified patent and that said Letters Patent is hereby corrected as shown below:

In the Claims

In Claim 1, Column 14, Line 6, please replace "though" with --through-- therefore.

Signed and Sealed this  
Nineteenth Day of March, 2019

Andrei Iancu  
*Director of the United States Patent and Trademark Office*